United States Patent [19]

Rodriguez et al.

[11] Patent Number: 4,494,481
[45] Date of Patent: Jan. 22, 1985

[54] ANIMAL LITTER COMPOSITION

[75] Inventors: Pedro A. Rodriguez; James B. Edwards, both of Cincinnati; Fred M. Habermehl, Hamilton, all of Ohio

[73] Assignee: The Procter & Gamble Company, Cincinnati, Ohio

[21] Appl. No.: 441,318

[22] Filed: Nov. 12, 1982

[51] Int. Cl.³ ............................................. A01K 1/015
[52] U.S. Cl. ...................................................... 119/1
[58] Field of Search .............................. 119/1; 502/84

[56] References Cited

U.S. PATENT DOCUMENTS

| | | | |
|---|---|---|---|
| 3,523,018 | 8/1970 | Geissler et al. | 71/28 |
| 3,789,797 | 2/1974 | Brewer | 119/1 |
| 3,909,454 | 9/1975 | Azrad | 502/84 X |
| 3,921,581 | 11/1975 | Brewer | 119/1 |
| 3,923,005 | 12/1975 | Fry et al. | 119/1 |
| 4,129,094 | 12/1978 | Stockel | 119/1 |
| 4,159,008 | 6/1979 | Bavaveas | 119/1 |
| 4,196,102 | 4/1980 | Inooka et al. | 502/84 X |
| 4,315,761 | 2/1982 | Larrson et al. | 119/1 X |
| 4,341,664 | 7/1982 | Antos | 502/84 X |
| 4,419,273 | 12/1983 | Santilli et al. | 502/84 X |

FOREIGN PATENT DOCUMENTS

| | | |
|---|---|---|
| 49-27035 | 7/1974 | Japan. |
| 1441232 | 6/1976 | United Kingdom. |
| 1581586 | 12/1980 | United Kingdom. |

OTHER PUBLICATIONS

Kaneshiro et al., *Arch. Biochem. Biophys.*, 174, 647–650, (1976).

Geike, *Z. Anal. Chem.*, Band 258, Heft 4, 284–285, (1972).

*Primary Examiner*—Hugh R. Chamblee
*Attorney, Agent, or Firm*—J. D. Schaeffer; S. J. Goldstein; J. C. Rasser

[57] ABSTRACT

Solid absorbent materials, having adsorbed thereto from about 50 ppm to about 3000 ppm of a soluble salt of a transition metal of Group Ib or Group IIb of the periodic table of the elements, when used as animal litter products, effectively prevent the development of urine odors.

18 Claims, No Drawings

ANIMAL LITTER COMPOSITION

TECHNICAL FIELD

This invention relates to an inexpensive absorbent animal litter product which is capable of preventing the development of unpleasant urine odors over an extended period of time.

The owners of household pets, in particular cats, perceive the development of urine odors in animal litter boxes as a significant problem. Attempts to alleviate this problem have ranged from the addition of a perfume to an absorbent animal litter product to processing alfalfa or another chlorophyll containing grass into an absorbent animal litter material. Both approaches are relatively expensive and have met with only limited success. Household pets tend to dislike the smell of such products and to avoid the use of the litter. Moreover, to the extent that these materials effectively mask or neutralize unpleasant odors, they are effective over only a limited period of time.

It is therefore an object of this invention to provide an absorbent animal litter material which prevents the development of unpleasant odors over an extended period of time. It is a further object of this invention to provide a method for preparing such an animal litter material.

BACKGROUND ART

Silver, copper, mercury, cadmium and zinc ions are known urease inhibitors; see, for example, Kaneshiro et al., *Arch. Biochem. Biophys.* 174 647–650 (1976) and Geike, *Z. Anal. Chem.* Band 258, Heft 4, 284–285 (1972). Practical applications disclosed include the quantitative analysis of these metals with urease (e.g. the Geike reference cited above), and the use of copper salts as additives to urea fertilizer to prevent its decomposition (U.S. Pat. No. 3,523,018, issued Aug. 4, 1970, to Geissler et al).

The use of copper and/or silver metal for preventing the development of malodors has been disclosed in British Pat. No. 1,581,586, issued Dec. 17, 1980 to Yamouchi (footwear comprising a resin containing powdered copper, silver or a Cu-Ag alloy); French Demande No. 2,259,620, published Aug. 29, 1975, Hansson (treatment of e.g., liquid cow manure with a solution containing $HNO_3$, a nitrite and $CuSO_4$); and Japanese Specification No. 74/27,035, July 13, 1974, Okahima, et al. (bentonite clay impregnated with $Cu(NO_3)_2$ and $AgNO_3$ and subsequently dried and oxidized, for use in tanks for carrying urine).

Prior art attempts to deodorize cat litter include the addition of a perfume (see, e.g., U.S. Pat. No. 3,921,581, issued Nov. 25, 1975 to Brewer), and the addition of chlorophyll, mainly in the form of dried alfalfa to the litter, (see, e.g., U.S. Pat. No. 3,923,005, issued Dec. 2, 1975 to Fry et al., assigned to The Clorox Company).

U.S. Pat. No. 4,129,094, issued Dec. 12, 1978 to Stockel, discloses the use of fly ash, bottom ash and/or boiler slag as cat litter materials. The composition of fly ash, as determined by the ASTM and cited in the patent, includes silicon dioxide, alumina, ferric oxide, calcium oxide, magnesium oxide, sodium oxide and potassium oxide. The material is not reported to contain any of the Group Ib or IIb transition metals.

SUMMARY OF THE INVENTION

This invention relates to a solid absorbent material useful as an animal litter, having adsorbed thereto from about 50 ppm to about 3000 ppm of a soluble salt of a transition metal of Group Ib or group IIb of the periodic table of the elements. The transition metals may be used at such low levels that neither their cost nor their toxicity creates any problems. The animal litter material of this invention effectively prevents the development of unpleasant odors over an extended period of time. This invention further encompasses a method of making the subject animal litter product.

DETAILED DESCRIPTION OF THE INVENTION

As used herein, gas concentrations are volume in volume, unless indicated otherwise. The amounts of transition metal are expressed in weight of the transition metal salt by weight of the absorbent material.

The transition metal salt is adsorbed to the solid absorbent material by contacting the solid absorbent material with a solution, preferably an aqueous solution, of the transition metal salt. "Contacting" means wetting at least a significant portion of the surface area of the solid absorbent material with the transition metal solution, and thus includes impregnating, soaking, and spraying.

The unpleasant odors associated with the urine of household pets is perceived as an important problem by the owners of such pets. It is therefore not surprising that the literature is replete with reports of attempts to alleviate this problem. Among the more notable examples are animal litter products to which perfume or chlorophyll has been added. The former may be in the form of encapsulated particles, the latter e.g. in the form of alfalfa pellets.

Although the odor problem has been addressed in various ways, little, if anything, appears to be known about its nature. It is commonly assumed that ammonia is the major component of malodorous materials emanating from urine. This suggests that urease, the enzyme that converts urea to ammonia, would be responsible for the odor development. However, it has surprisingly been found that reducing ammonia levels to well below the olfactory detection threshold (ODT) does not eliminate the odor problem. It is being hypothesized that sulfides and mercaptans, which have olfactory detection thresholds in the ppb, or even ppt, range greatly contribute to the malodor generally associated with animal litter boxes. The ODT of ammonia is much higher than that: ca. 50 ppm. See "Compilation of Odor and Taste Threshold Values Data", W. H. Stoke, ed., ASTM data series DS 48. In order to effectively prevent the development of malodors, an animal litter material must therefore be capable of eliminating sulfide and mercaptan odors. The capability of eliminating ammonia odor is of only secondary importance and may not be important at all, as it is unlikely that the amount of ammonia generated will exceed the ODT under normal conditions in the typical home.

It has now been found that when a normal absorbent animal litter material as is commercially available is contacted with an aqueous solution of a salt of a transition metal of group Ib or group IIb of the periodic table and is subsequently dried, an animal litter material is obtained which is capable of effectively preventing the development of unpleasant odors in animal litter boxes over a period of three weeks or more. It has further been discovered that effective odor prevention is obtained with very small amounts, from 50 ppm to about 3000 ppm, of the transition metal salt. This is particularly important because most of these transition metals are very toxic and/or very expensive. One of the most important aspects of this invention is that expensive and toxic materials can be used at such low levels that an effective product is obtained without cost or toxicity being factors of any importance. The low levels of transition metal salt are effective only if they are adsorbed to the absorbent material. If the salt is added as a pulverized or crystalline material in a dry form to the litter material no appreciable prevention of odor development is obtained, even if substantially higher levels of transition metal salt are used.

Any absorbent solid material suitable for use as an animal litter is suitable for use in the present invention. Suitable examples include minerals, typically clay such as kaolinites, montmorillonites, or bentonites; fly ash as obtained from the burning of coal; but also absorbent fibrous webs like cellulosic webs or polymeric fibrous webs; pelletized absorbent materials (e.g. sawdust or polyurethane foam); and the like. Alternatively, pellets of a cation exchange resin can be loaded with transition metal ions by cation exchange; these pellets, when mixed with a conventional animal litter product, will effectively prevent the development of malodors. Particle sizes typically range from about 0.1 inch to about 0.5 inch (from about 0.25 cm to about 1.3 cm). Other examples of suitable solid absorbent materials are disclosed in U.S. Pat. No. 3,921,581, issued Nov. 25, 1975 to Brewer, incorporated herein by reference.

Since the method of preparing the animal litter products of the present invention involves contacting the solid absorbent material with, preferably, an aqueous solution of the transition metal ion, suitable sources of the transition metal ion are its soluble salts. Suitable examples are silver chlorate, silver nitrate, mercury acetate, mercury chloride, mercury nitrate, copper metaborate, copper bromate, copper bromide, copper chloride, copper dichromate, copper nitrate, copper salicylate, copper sulfate, zinc acetate, zinc borate, zinc bromate, zinc bromide, zinc chlorate, zinc chloride, zinc sulfate, cadmium acetate, cadmium borate, cadmium bromide, cadmium chlorate, cadmium chloride, cadmium formate, cadmium iodate, cadmium iodide, cadmium permanganate, cadmium nitrate, cadmium sulfate, and gold chloride.

Animal litter products according to the present invention can be prepared as follows. The calculated amount of transition metal salt is dissolved in an amount of water which is sufficient to completely saturate the solid absorbent material. The amount of water necessary will vary with the kind of absorbent material used and typically is in the range of from about 1 liter to about 5 liters per kg of solid absorbent material. The solid absorbent material is slurried with the transition metal salt solution. The slurry is then allowed to equilibrate for about 10 minutes. The slurry may be agitated by stirring or by vibrating which reduces the amount of time needed for equilibration. Subsequently, the water is drained off and the wet solid material is collected on e.g., a screen. The solid material is then dried at ambient conditions, or in an oven at a temperature of from about 50° C. to about 95° C. This procedure lends itself extremely well to a continuous process, whereby metered flows of solid absorbent material and transition metal solution are contacted with each other, the material is subsequently drained on a perforated conveyor belt and dried in an air-dry tunnel. The amount of transition metal salt on the absorbent material may be determined by direct analysis, or by analyzing the drained-off solution and calculating the mass balance. The amount of solution may be such that it is just sufficient to saturate the absorbent material so that no draining step will be necessary. This insures quantitative deposition of the transition metal salt and eliminates the necessity of handling excess water. An important aspect of this invention is that the transition metal salt need not be fixed to the absorbent material by calcination, or be converted to its oxide. This is important because it eliminates an energy intensive, and therefore costly, process step and it also makes the process of this invention suitable for absorbent materials which are not heat resistant like cellulose fibers, polymeric fibers and polyurethane foam pellets.

The amount of transition metal salt to be used depends on its effectiveness, its cost and its toxicity. Silver salts and mercury salts are very effective but are also toxic and expensive and are therefore used at levels ranging from about 50 ppm to about 500 ppm, preferably from about 100 ppm to about 300 ppm. Copper salts, zinc salts and cadmium salts are most effectively used at levels ranging from about 1500 ppm to about 3000 ppm, preferably at levels from about 1800 ppm to about 2500 ppm. Gold salts are effective and substantially less toxic than silver or mercury. However, under prevailing economic circumstances it is doubtful that the use of gold salts would ever be economically feasible.

ODOR DEVELOPMENT TEST

Samples of a commercial clay cat litter product (Cat's Pride, from Oil-Dri Corporation of America, Chicago, Ill.) were treated with solutions of transition metal salts by the batch method described above at the rate of 1 liter solution per 1135 g of clay. The samples were stirred until the litter was thoroughly saturated with the entire solution. The wet material was then dried in an oven at 93° C. 15 g of the litter product were weighed into a container and treated with 15 ml of cat urine. (If catheterized cat urine was used *Proteus vulgaris* was added, as *Proteus vulgaris* is present in normal cat urine and not in catheterized cat urine). The container was closed and the head space above the litter material was analyzed for ammonia and sniffed for odor development by two independent panelists once every weekday after start of the test. The results are summarized in the table below. The controls were run with untreated samples of Cat's Pride clay litter.

Test 1

| Day | Control $NH_3$ (ppm) | odor | 50 ppm $AgNO_3$ $NH_3$ (ppm) | odor | 200 ppm $AgNO_3$ $NH_3$ (ppm) | odor | 500 ppm $AgNO_3$ $NH_3$ (ppm) | odor |
|---|---|---|---|---|---|---|---|---|
| 7 | 3 | — | 0 | — | 0 | — | 0 | — |
| 8 | 3 | — | 0 | — | 0 | — | 0 | — |
| 9 | 5 | — | 0 | — | 0 | — | 0 | — |
| 13 | 35 | + | 10 | — | 0 | — | 0 | — |
| 14 | 50 | ++ | 10 | — | 0 | — | 0 | — |
| 15 | 60 | +++ | 20 | — | 0 | — | 5 | — |
| 16 | 80 | +++ | a | + | a | — | a | — |
| 21 | 150 | +++ | 100 | + | 0 | — | 2.5 | — |

— no odor detectable
+ detectable odor
++ strong odor
+++ very strong odor
a not measured Test 2

| Day | Control NH$_3$ (ppm) | Control odor | 200 ppm CuSO$_4$ NH$_3$ (ppm) | 200 ppm CuSO$_4$ odor | 2000 ppm CuSO$_4$ NH$_3$ (ppm) | 2000 ppm CuSO$_4$ odor | 200 ppm HgCl$_2$ NH$_3$ (ppm) | 200 ppm HgCl$_2$ odor | 2000 ppm HgCl$_2$ NH$_3$ (ppm) | 2000 ppm HgCl$_2$ odor |
|---|---|---|---|---|---|---|---|---|---|---|
| 6  | 2   | −   | 5   | − | 0   | − | 0   | − | 0   | − |
| 7  | 50  | ++  | 5   | − | 10  | − | 0   | − | 0   | − |
| 8  | 210 | +++ | 5   | − | 10  | − | 2.5 | − | 2.5 | − |
| 9  | 600 | +++ | a   | − | a   | − | a   | − | a   | − |
| 14 | 520 | +++ | 10  | − | 40  | − | 0   | − | 10  | − |
| 15 | 520 | +++ | 38  | + | 60  | + | 0   | − | 25  | − |
| 16 | 600 | +++ | 40  | + | 70  | + | 0   | − | 30  | − |

− no odor detectable
+ detectable odor
++ strong odor
+++ very strong odor
$^a$not measured Small amounts of salts of transition metals from group Ib or IIb of the periodic table effectively prevent the development of unpleasant odors and the development of ammonia over a period of 16 days or more whereas untreated control samples started to develop a very strong pungent odor and significant amounts of ammonia after a period of 7–9 days.

By the method described above, the following absorbent solid materials, having soluble transition metal salts adsorbed thereto, are prepared: bentonite clay+500 ppm silver chloride; fly ash pellets (ca 1 cm particle size)+300 ppm mercury nitrate; cellulose fiber web+2000 ppm copper (II) chloride; sawdust pellets (ca 0.5 cm particle size)+2500 ppm zinc sulfate; and polyurethane foam pellets (ca 0.8 cm particle size)+1800 ppm cadmium nitrate.

When used as animal litter products, these absorbent solid materials effectively prevent the development of urine odors.

What is claimed is:

1. A solid absorbent material useful as an animal litter, having adsorbed thereto from about 50 ppm to about 3000 ppm of a soluble salt of a transition metal of Group Ib or Group IIb of the periodic table of the elements.

2. The solid absorbent material of claim 1 which has adsorbed thereto from about 50 ppm to about 500 ppm of a soluble salt of silver or mercury.

3. The solid absorbent material of claim 2 which has adsorbed thereto from about 100 ppm to about 300 ppm of a soluble salt of silver or mercury.

4. The solid absorbent material of claim 2 wherein the soluble salt is silver nitrate.

5. The solid absorbent material of claim 2 wherein the soluble salt is mercury chloride.

6. The solid absorbent material of claim 1 which has adsorbed thereto from about 1500 ppm to about 3000 ppm of a soluble salt of copper, zinc, or cadmium.

7. The solid absorbent material of claim 6 which has adsorbed thereto from about 1800 ppm to about 2500 ppm of a soluble salt of copper, zinc, or cadmium.

8. The solid absorbent material of claim 6 wherein the soluble salt is copper sulfate.

9. The solid absorbent material of claim 6 wherein the soluble salt is zinc sulfate.

10. An absorbent clay material useful as an animal litter, which has adsorbed thereto from about 50 ppm to about 3000 ppm of a soluble salt of a transition metal of group Ib or group IIb of the periodic table of the elements.

11. A method for preparing an animal litter product from a solid absorbent material, comprising the steps of:
   (a) dissolving from about 50 ppm to about 3000 ppm by weight of the solid absorbent material of a soluble salt of a transition metal of group Ib or group IIb of the periodic table of the elements in water;
   (b) soaking the solid absorbent material in the aqueous transition metal salt solution; and
   (c) drying the solid absorbent material, provided that the transition metal salt is not fixed to the absorbent material by calcination or converted to its oxide.

12. The method as described in claim 11, wherein the solid absorbent material is a clay.

13. The method as described in claim 11, wherein the soluble transition metal salt is a soluble silver salt.

14. The method of claim 13, wherein the amount of silver salt is from about 50 ppm to about 500 ppm by weight of the solid absorbent material.

15. The method of claim 14, wherein the amount of soluble silver salt is from about 100 ppm to about 300 ppm.

16. The method of claim 11, wherein the soluble transition metal salt is a soluble zinc salt.

17. The method of claim 16, wherein the amount of soluble zinc salt is from about 1500 ppm to about 3000 ppm by weight of the solid absorbent material.

18. The method of claim 16, wherein the amount of soluble zinc salt is from about 1800 ppm to about 2500 ppm by weight of the solid absorbent material.

* * * * *